United States Patent [19]

Hettiarachchi

[11] Patent Number: 5,448,605
[45] Date of Patent: Sep. 5, 1995

[54] PALLADIUM ACETYLACETONATE SOLUTION AND RELATED METHOD OF MANUFACTURE

[75] Inventor: Samson Hettiarachchi, Menlo Park, Calif.

[73] Assignee: General Electric Company, San Jose, Calif.

[21] Appl. No.: 143,514

[22] Filed: Oct. 29, 1993

[51] Int. Cl.⁶ ............................................. B01J 27/20
[52] U.S. Cl. .................................. 376/305; 252/308; 252/310; 252/311; 252/364; 252/400.61
[58] Field of Search ............... 252/308, 310, 311, 364, 252/400.61; 376/305

[56] References Cited

U.S. PATENT DOCUMENTS

| | | | |
|---|---|---|---|
| 3,943,053 | 3/1976 | Kovach et al. | 208/143 |
| 4,093,559 | 6/1978 | Fernholz et al. | 252/443 |
| 4,324,676 | 4/1982 | Gilbert | 252/79 |
| 4,431,574 | 2/1984 | Bournonville et al. | 502/261 |
| 5,100,693 | 3/1992 | Eisch et al. | 427/54.1 |
| 5,130,081 | 7/1992 | Niedrach | 376/305 |
| 5,135,709 | 8/1992 | Andresen et al. | 376/305 |

FOREIGN PATENT DOCUMENTS

| | | |
|---|---|---|
| 0450440 | 10/1991 | European Pat. Off. |
| 0450444 | 10/1991 | European Pat. Off. |
| 0484808 | 5/1992 | European Pat. Off. |
| 0514089 | 11/1992 | European Pat. Off. |
| 3443927 | 6/1986 | Germany . |
| 4113525 | 10/1992 | Germany . |

OTHER PUBLICATIONS

3rd Symposium on Chemical Perspectives of Microelectronics Material, Boston, USA, Nov. 30–Dec. 3, 1992, Mat. Res. Soc. Symp. Proc. vol. 282, pp. 353–358, Kowalczyk et al., "Characterization of Palladium Acetylacetonate as a CVD Precursor for Pd Metallization".
"Effect of Palladium Coatings on the Corrosion Potential of Stainless Steel etc.," L. W. Niedrach, Corrosion, vol. 47, No. 3, 162–169 (Mar. 1991).
Database WPI, Week 8840, Derwent Publ. Ltd., London, GB; AN 88–282089 & JP-A-63 206 485 (Nippon Radiator).
Patent Abstracts of Japan, vol. 18, No. 344 (C-1218), Jun. 29, 1994 & JP-A-06 081 159 (Japan Energy Corp.), Mar. 22, 1994.
Miscellaneous abstracts (2 pages).

*Primary Examiner*—Donald P. Walsh
*Attorney, Agent, or Firm*—James E. McGinness

[57] ABSTRACT

A solution or suspension for reducing corrosion of stainless steel components in a water-cooled nuclear reactor. A compound containing a platinum group metal, e.g., palladium, is dissolved in an ethanol/water mixture or suspended in water. The resulting solution or suspension is injected into the water of the reactor. This compound has the property that it decomposes under reactor thermal conditions to release ions/atoms of the platinum group metal which incorporate in or deposit on the oxide film formed on the stainless steel reactor components. The compound may be organic, organometallic (e.g., palladium acetylacetonate) or inorganic in nature.

12 Claims, 5 Drawing Sheets

PALLADIUM ACETYLACETONATE SOLUTION AND RELATED METHOD OF MANUFACTURE

FIELD OF THE INVENTION

This invention relates to reducing the corrosion potential of components exposed to high-temperature water. As used herein, the term "high-temperature water" means water having a temperature of about 150° C. or greater, steam, or the condensate thereof. High-temperature water can be found in a variety of known apparatus, such as water deaerators, nuclear reactors, and steam-driven power plants.

BACKGROUND OF THE INVENTION

Nuclear reactors are used in central-station electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about $-230$ to $-300$ mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

Corrosion potentials of stainless steels in contact with reactor water containing oxidizing species can be reduced below the critical potential by injection of hydrogen into the water so that the dissolved concentration is about 50 to 100 ppb or greater. For adequate feedwater hydrogen addition rates, conditions necessary to inhibit IGSCC can be established in certain locations of the reactor. Different locations in the reactor system require different levels of hydrogen addition. Much higher hydrogen injection levels are necessary to reduce the ECP within the high radiation flux of the reactor core, or when oxidizing cationic impurities, e.g., cupric ion, are present.

It has been shown that IGSCC of Type 304 stainless steel used in BWRs can be mitigated by reducing the ECP of the stainless steel to values below $-0.230$ V(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or any other platinum group metal. The presence of palladium on the stainless steel surface reduces the hydrogen demand to reach the required IGSCC critical potential of $-0.230$ V(SHE). The techniques used to date for palladium coating include electroplating, electroless plating, plasma deposition and related high-vacuum techniques. Palladium alloying has been carried out using standard alloy preparation techniques. Both of these approaches are ex-situ techniques in that they cannot be practiced while the reactor is in operation.

U.S. Pat. No. 5,135,709 to Andresen et al. discloses a method for lowering the ECP on components formed from carbon steel, alloy steel, stainless steel, nickel-based alloys or cobalt-based alloys which are exposed to high-temperature water by forming the component to have a catalytic layer of a platinum group metal. As used therein, the term "catalytic layer" means a coating on a substrate, or a solute in an alloy formed into the substrate, the coating or solute being sufficient to catalyze the recombination of oxidizing and reducing species at the surface of the substrate; and the term "platinum group metal" means metals from the group consisting of platinum, palladium, osmium, ruthenium, iridium, rhodium, and mixtures thereof.

In nuclear reactors, ECP is further increased by higher levels of oxidizing species, e.g., up to 200 ppb or greater of oxygen in the water, from the radiolytic decomposition of water in the core of the nuclear reactor. The method disclosed in U.S. Pat. No. 5,135,709 further comprises providing a reducing species in the high-temperature water that can combine with the oxidizing species. In accordance with this known method, high concentrations of hydrogen, i.e., about 100 ppb or more, must be added to provide adequate protection to materials out of the reactor core, and still higher concentrations are needed to afford protection to materials in the reactor core. It is also known that platinum or palladium can be added to increase the ECP of stainless steel exposed to deaerated acidic aqueous solutions, thereby forming a passive oxide layer on the stainless steel and reducing further corrosion.

The formation of a catalytic layer of a platinum group metal on an alloy from the aforementioned group catalyzes the recombination of reducing species, such as hydrogen, with oxidizing species, such as oxygen or hydrogen peroxide, that are present in the water of a BWR. Such catalytic action at the surface of the alloy can lower the ECP of the alloy below the critical potential where IGSCC is minimized. As a result, the efficacy of hydrogen additions to high-temperature water in lowering the ECP of components made from the alloy and exposed to the injected water is increased manyfold. Furthermore, it is possible to provide catalytic activity at metal alloy surfaces if the metal substrate of such surfaces contains a catalytic layer of a platinum group metal. Relatively small amounts of the platinum group metal are sufficient to provide the catalytic layer and catalytic activity at the surface of the metal substrate. For example, U.S. Pat. No. 5,135,709 teaches that a solute in an alloy of at least about 0.01 wt %, preferably at least 0.1 wt % provides a catalytic layer sufficient to lower the ECP of the alloy below the critical potential. The solute of a platinum group metal can be present up to an amount that does not substantially impair the metallurgical properties, including strength, ductility, and toughness of the alloy. The solute can be provided by methods known in the art, for example by addition to a melt of the alloy or by surface alloying. In addition, a coating of the platinum group metal, or a coating of an alloy comprised of a solute of the platinum group metal as described above, provides a catalytic layer and catalytic activity at the surface of the metal. Suitable coatings can be deposited by methods well known in the art for depositing substantially continuous coatings on metal substrates, such as plasma spraying, flame spraying, chemical vapor deposition, physical vapor deposition processes such as sputtering, welding such as metal inert gas welding, electroless plating, and electrolytic plating.

Thus, lower amounts of reducing species such as hydrogen are effective to reduce the ECP of the metal components below the critical potential, because the efficiency of recombination of oxidizing and reducing species is increased manyfold by the catalytic layer. Reducing species that can combine with the oxidizing species in the high-temperature water are provided by conventional means known in the art. In particular, reducing species such as hydrogen, ammonia, or hydrazine are injected into the feedwater of the nuclear reactor.

SUMMARY OF THE INVENTION

The present invention improves upon the teachings of U.S. Pat. No. 5,135,709 by allowing the achievement of specified HWC conditions at key locations in the reactor system by addition of only low (or even no) hydrogen to the feedwater. Thus, the negative side effect of high main steam line radiation increase can be avoided. In addition, the amount of hydrogen required and associated costs will be reduced significantly.

The present invention is a solution or suspension of a compound containing a metal which improves the corrosion resistance of stainless steel components when the oxided surfaces of those components are doped or coated with the metal. The compound is injected in situ into the high-temperature reactor water. The preferred compound for this purpose is palladium acetylacetonate, an organometallic compound. The concentration of palladium in the reactor water is preferably in the range of 5 to 100 ppb. Upon injection, the palladium acetylacetonate decomposes and deposits palladium on the oxided surface.

The palladium gets incorporated into the stainless steel oxide film via a thermal decomposition process of the organometallic compound wherein palladium ions/atoms apparently replace iron, nickel and/or chromium atoms in the oxide film, resulting in a palladium-doped oxide film. Alternatively, palladium may be deposited within or on the surface of the oxide film in the form of a finely divided metal. The oxide film is believed to include mixed nickel, iron and chromium oxides.

The ECPs of the stainless steel components should all drop by −300 mV after palladium injection. It is possible to reduce the ECP of Type 304 stainless steel to IGSCC protection values without injecting hydrogen provided that organics are present in the water. This occurs because of the catalytic oxidation of organics on palladium-doped surfaces.

In accordance with a preferred embodiment of the invention, a metal acetylacetonate powder is dissolved in ethanol and the resulting solution is diluted with water. Alternatively, the metal acetylacetonate powder can be mixed with water alone (without ethanol) to form a suspension.

Other palladium compounds of organic, organometallic or inorganic nature, as well as compounds of other platinum group metals or non-platinum group metals such as titanium and zirconium, can also be used.

DETAILED DESCRIPTION OF THE PREFERRED EMBODIMENTS

Figure 1:
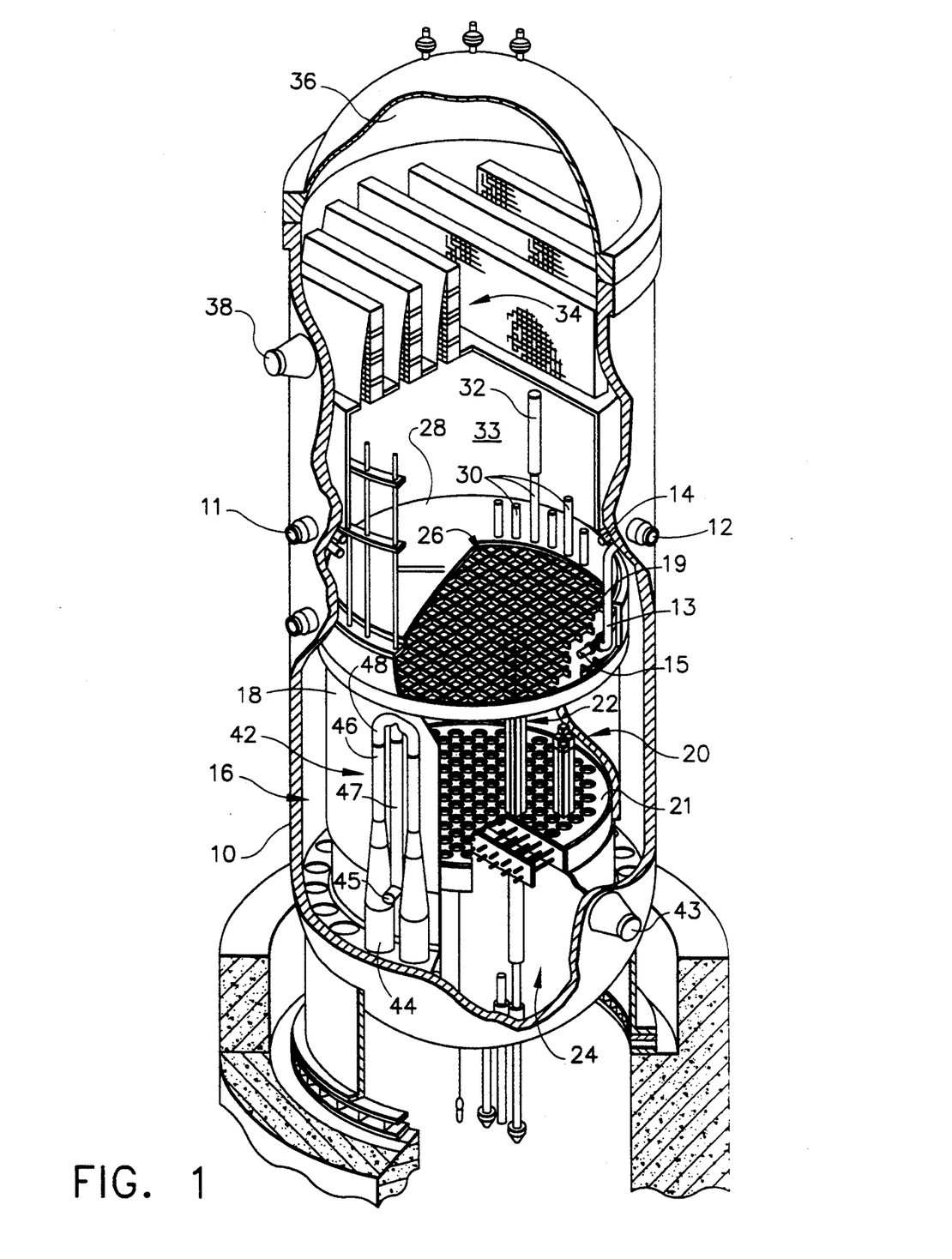
FIG. 1 is a schematic showing a partially cutaway perspective view of a conventional BWR.

The fluid flow in a boiling water reactor will be generally described with reference to FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. A core spray inlet 11 supplies water to a core spray sparger 15 via core spray line 13. The feedwater from feedwater sparger 14 flows downwardly through the downcomer annulus 16, which is an annular region between RPV 10 and core shroud 18. Core shroud 18 is a stainless steel cylinder which surrounds the core 20 comprising numerous fuel assemblies 22 (only two 2×2 arrays of which are depicted in FIG. 1). Each fuel assembly is supported at the top by top guide 19 and at the bottom by core plate 21. Water flowing through downcomer annulus 16 then flows to the core lower plenum 24.

The water subsequently enters the fuel assemblies 22 disposed within core 20, wherein a boiling boundary layer (not shown) is established. A mixture of water and steam enters core upper plenum 26 under shroud head 28. Core upper plenum 26 provides standoff between the steam-water mixture exiting core 20 and entering vertical standpipes 30, which are disposed atop shroud head 28 and in fluid communication with core upper plenum 26.

The steam-water mixture flows through standpipes 30 and enters steam separators 32, which are of the axial-flow centrifugal type. The separated liquid water then mixes with feedwater in the mixing plenum 33, which mixture then returns to the core via the downcomer annulus. The steam passes through steam dryers 34 and enters steam dome 36. The steam is withdrawn from the RPV via steam outlet 38.

The BWR also includes a coolant recirculation system which provides the forced convection flow through the core necessary to attain the required power density. A portion of the water is sucked from the lower end of the downcomer annulus 16 via recirculation water outlet 43 and forced by a centrifugal recirculation pump (not shown) into jet pump assemblies 42 (only one of which is shown) via recirculation water inlets 45. The BWR has two recirculation pumps, each of which provides the driving flow for a plurality of jet pump assemblies. The pressurized driving water is supplied to each jet pump nozzle 44 via an inlet riser 47, an elbow 48 and an inlet mixer 46 in flow sequence. A typical BWR has 16 to 24 inlet mixers.

The present invention is a solution or suspension of a compound containing a metal, preferably palladium, which improves the corrosion resistance of stainless steel components when the oxided surfaces of those components are doped or coated with the metal. The solution or suspension can be injected in situ into the high-temperature water of a BWR. Preferably the palladium compound is injected at a point upstream of the feedwater inlet 12 (see FIG. 1). The high temperatures as well as the gamma and neutron radiation in the reactor core act to decompose the compound, thereby freeing palladium ions/atoms for deposition on the surface of the oxide film. One Pd-containing compound successfully used for this purpose is an organometallic compound, palladium acetylacetonate. However, other palladium compounds of organic, organometallic and inorganic nature can also be used for this purpose.

Tests were conducted which proved that the present method for depositing palladium on or incorporating palladium in the stainless steel surfaces of a BWR is feasible. Moreover, it has been shown that after palladium treatment in accordance with the invention, the ECP value of the stainless steel surfaces remains quite negative and below the required IGSCC critical potential of −0.230 V(SHE) even without the addition of any hydrogen, provided that organics are present in the water. This phenomenon has been neither reported nor observed previously. Thus, the invention consists of two parts: (1) an in-situ method for depositing palladium (or other metal) on oxided stainless steel surfaces while the reactor is operating; and (2) a method that makes the IGSCC critical potential achievable without injecting hydrogen into the water if organics are present in the water.

An experiment was performed to determine the feasibility of depositing palladium on Type 304 stainless steel by injecting an organometallic palladium compound, i.e., palladium acetylacetonate, into an autoclave that formed part of a high-temperature recirculating flow loop. The autoclave had a constant extension rate test (CERT) specimen made of Type 304 stainless steel and a stainless steel tip electrode also made of Type 304 stainless steel. The reference electrodes used to measure ECPs consisted of a $Cu/Cu_2O/ZrO_2$ type reference electrode and an external pressure balanced Ag/AgCl, 0.1M KCl reference electrode. The recirculating flow loop contained deionized water heated to 550° F. inside the autoclave. The oxygen level in the effluent water was 170 ppb and the CERT specimen potential at this oxygen level was +0.042 V(SHE).

The palladium acetylacetonate injection solution was prepared by dissolving 52.6 mg of palladium acetylacetonate powder in 40 ml of ethanol. The ethanol solution is then diluted with water. After dilution, 10 ml of ethanol are added to the solution. This is then diluted to a volume of 1 liter. Alternatively, a water-based suspension can be formed, without using ethanol, by mixing palladium acetylacetonate powder in water. To improve the stability of the suspension, ultrasonication can be used to break down the particles.

The palladium acetylacetonate compound, dissolved in the ethanol/water mixture, was injected into the inlet side of the main pump in the flow loop using an injection pump at a rate of 0.4 cc/min so that the solution entering the autoclave (at 550° F.) had a palladium concentration of ~50 ppb.

Figure 2:
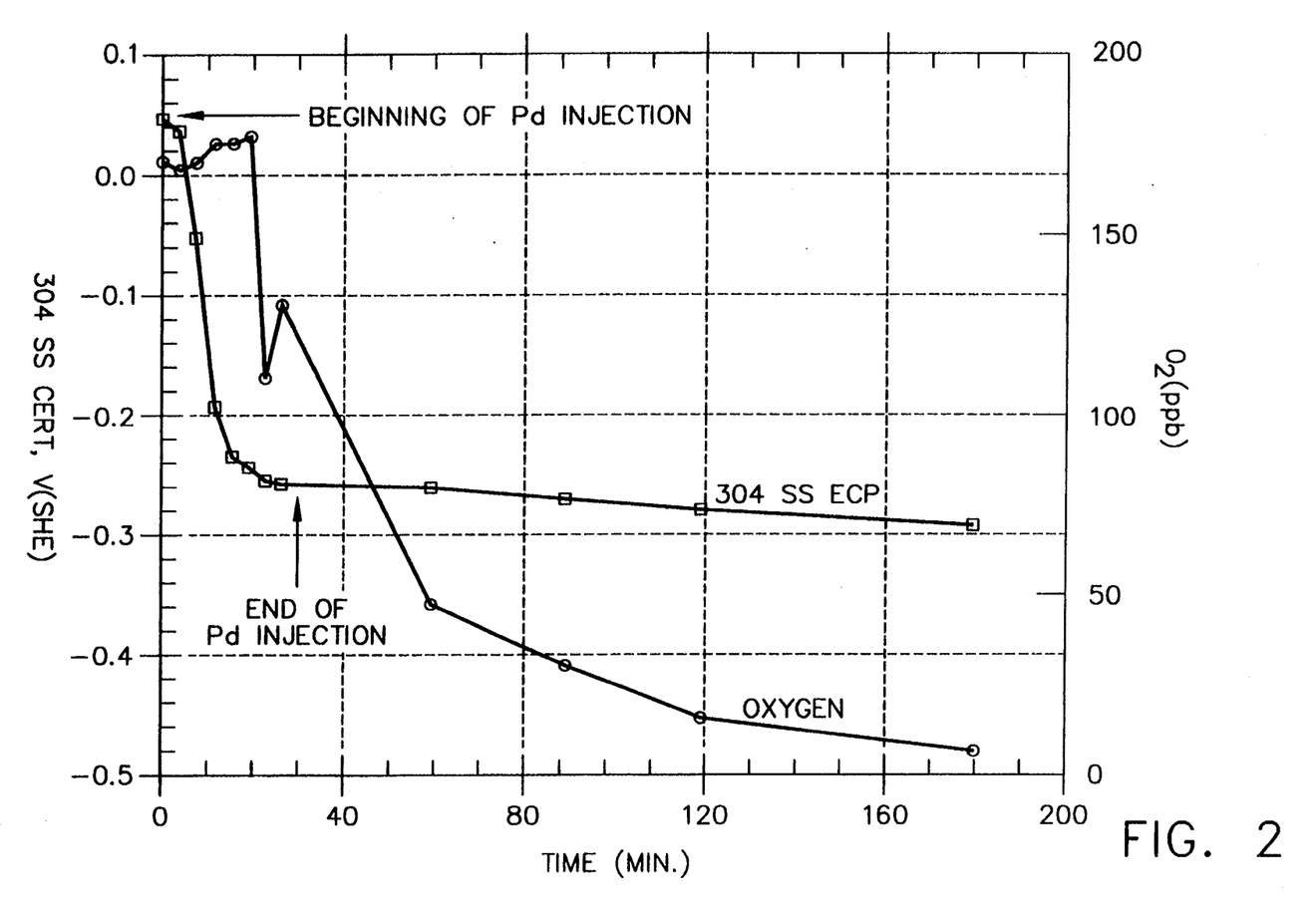
FIG. 2 is a plot showing the variation of the oxygen level of effluent water and the specimen ECP over time during and after the injection of palladium into an autoclave forming a part of a high-temperature recirculating flow loop.

As the palladium was being injected, within 30 minutes the ECP of the Type 304 stainless steel CERT sample dropped from +0.042 V(SHE) to −0.256 V(SHE). The effluent oxygen content also dropped as palladium was getting into the loop. The palladium injection was stopped after 30 minutes, but the ECP of the Type 304 stainless steel CERT specimen continued to drop slowly with time (see FIG. 2). The effluent oxygen content also continued to drop to sub-ppb levels despite the fact that the dissolved oxygen in the inlet water was ~320 ppb (calculated from the gas composition). During the palladium injection time, the stainless steel tip electrode potential dropped from −0.007 V(SHE) to −0.329 V(SHE), and the autoclave potential dropped from +0.048 V(SHE) to −0.257 V(SHE). In all cases the potentials continued to drop slowly even after the palladium injection had been discontinued.

The following conclusions were drawn from experimental data:

(1) The palladium either deposits or gets incorporated into the stainless steel oxide film via a thermal decomposition process of the organometallic compound. As a result of that decomposition, palladium ions/atoms become available to replace atoms, e.g., iron atoms, in the oxide film, thereby producing a palladium-doped oxide film on stainless steel.

(2) The potentials of the Type 304 stainless steel CERT specimen, the Type 304 stainless steel electrode tip and the autoclave all dropped by −300 mV after palladium injection.

(3) Although the oxygen content of the water entering the loop was high (−320 ppb), the effluent oxygen content dropped to sub-ppb levels because oxygen was consumed by the organics at the hot stainless steel surfaces. The organics were oxidized to form acetates/formates, as confirmed by ion chromatography.

(4) It is possible to reduce the potential of Type 304 stainless steel to IGSCC protection values without using hydrogen if organics are present in the water.

Figure 3:
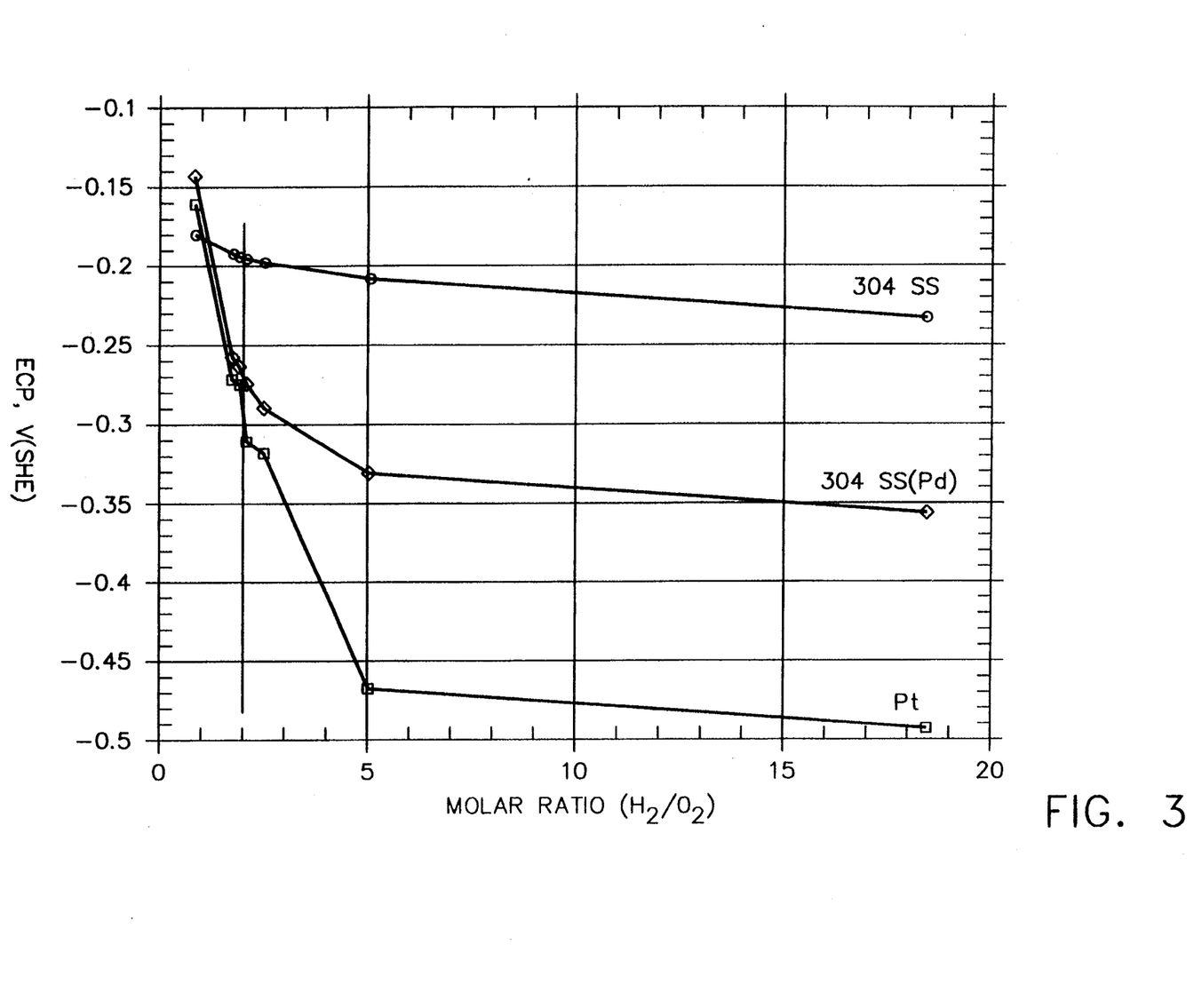
FIG. 3 is a plot showing the ECPs of platinum, lightly oxidized Type 304 stainless steel and palladium-doped Type 304 stainless steel as a function of the molar ratio of hydrogen to oxygen. In this case, palladium doping was performed for 30 minutes.

(5) The ECPs for platinum, palladium-doped Type 304 stainless steel (30 minutes of Pd injection) and lightly oxidized Type 304 stainless steel without palladium doping were determined as a function of the molar ratio of $H_2$ to $O_2$ dissolved in water. As can be seen in FIG. 3, the ECP for palladium-doped Type 304 stainless steel goes more negative than the ECP for undoped Type 304 stainless steel as the amount of $H_2$ increases. However, the ECP for the doped stainless steel was not as low as the ECP for platinum. The ECP for palladium-doped Type 304 stainless steel is below the critical potential when the molar ratio of $H_2/O_2=2$, at which point the palladium doping is not yet optimized.

Figure 4:
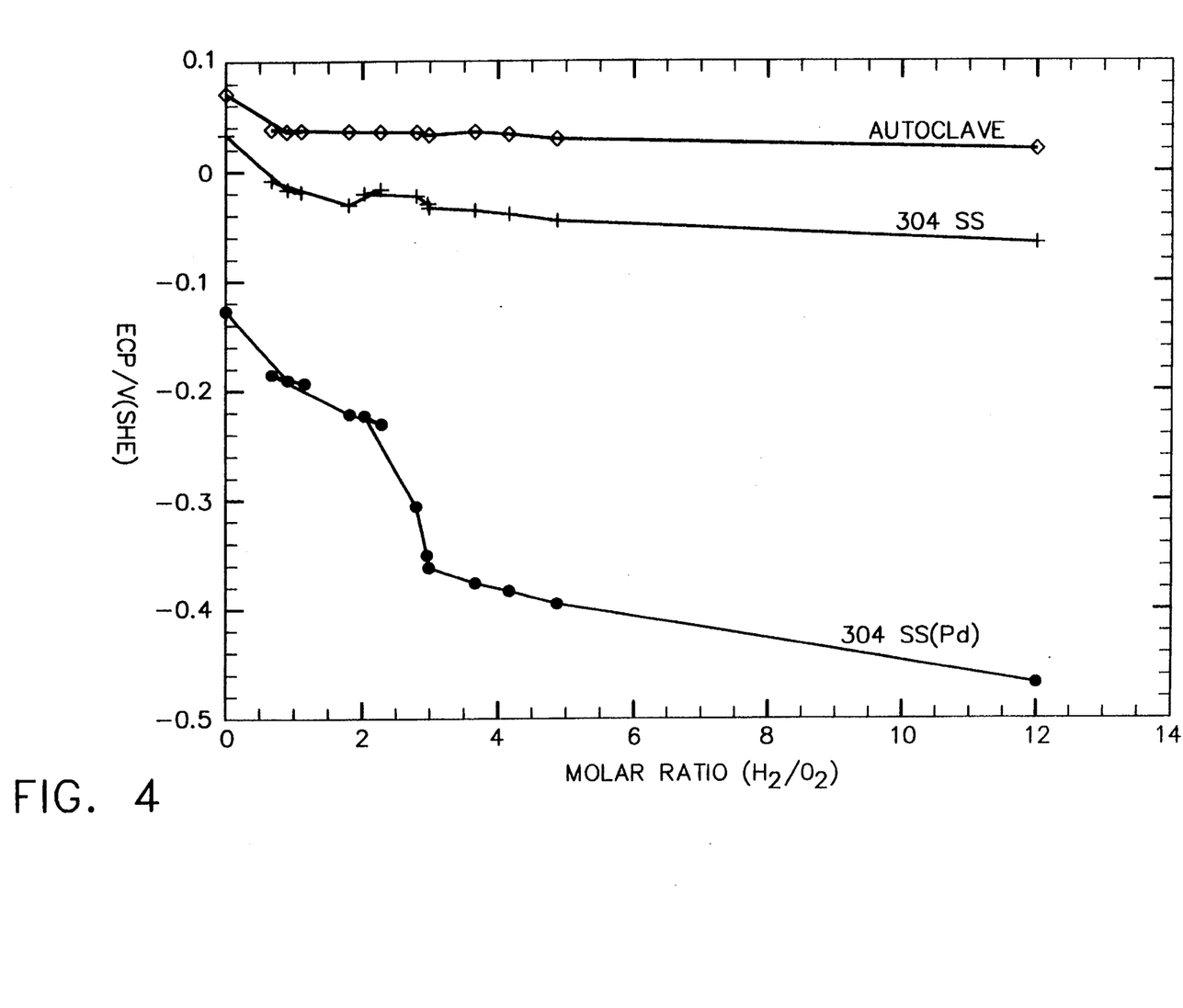
FIG. 4 is a plot showing the ECPs of well oxidized Type 304 stainless steel, palladium-doped Type 304 stainless steel and a Type 304 stainless steel autoclave as a function of the molar ratio of hydrogen to oxygen. In this case, palladium doping was performed for 48 hr.

(6) The ECPs for a Type 304 stainless autoclave, palladium-doped Type 304 stainless steel (48 hr of Pd injection) and well-oxidized Type 304 stainless steel without palladium doping were determined as a function of the molar ratio of $H_2$ to $O_2$ dissolved in water. As can be seen in FIG. 4, the ECP for Pd-doped Type 304 stainless steel goes more negative than the ECP for undoped Type 304 stainless steel as the amount of $H_2$ increases.

Figure 5:
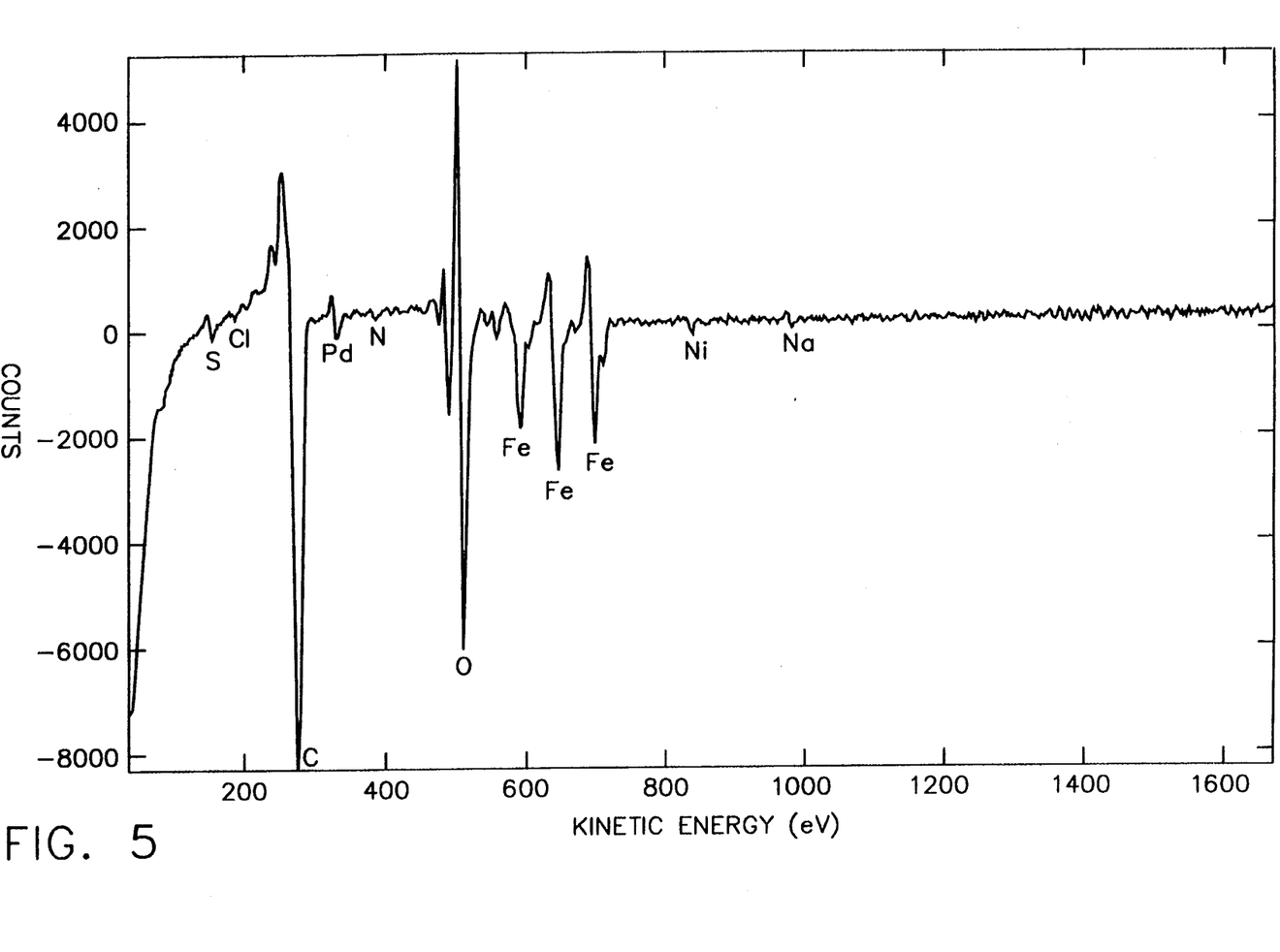
FIG. 5 shows an analysis of the Type 304 stainless steel surface after palladium doping for 48 hr.

(7) The data in FIG. 5 confirm the presence of palladium on the surface of the Type 304 stainless steel doped with palladium for 48 hr. Table I provides the surface concentration of palladium, which is 0.8 atomic %, and other elements for stainless steel doped with palladium for 48 hr. The dashes indicate no observation of a signal.

TABLE I

| Spectrum No. | Etch Depth | Na | Ni | Fe | Cr | O | N | Pd | C | Cl | S | Al |
|---|---|---|---|---|---|---|---|---|---|---|---|---|
| 1 | 0 | 0.5 | 0.8 | 15 | — | 21 | 0.8 | 0.8 | 61 | 0.1 | 0.5 | — |
| 2 | 1000 Å | — | 3.6 | 37 | 7.0 | 46 | — | — | 1.5 | — | — | 5.2 |

The present invention offers the advantage that Type 304 stainless steel surfaces can be coated or doped with palladium using an in-situ technique (while the reactor is operating) which is simple in application and also inexpensive. However, the technique is not limited to in-situ application. The application technology can be implemented even for coating ex-situ components. The technique can be applied to operating BWRs and PWRs and their associated components, such as steam generators. In practice, the palladium concentration in the reactor water is preferably in the range of 5 to 100 ppb.

The invention is advantageous in that IGSCC critical potential can be achieved without the addition of hydrogen if organics are present in the water. Furthermore, when hydrogen addition is required, the amount of hydrogen needed is minimized so that the main steam line radiation dose rates do not reach undesirable levels. The technology of the invention is unique because it can be applied during operation of a reactor and is simple when compared with other standard technologies such as electroplating, electroless plating, and plasma deposition, which require complex equipment and tooling.

The foregoing solution or suspension of palladium acetylacetonate has been disclosed for the purpose of illustration. Other metal acetylacetonates suitable for the purpose of enhancing corrosion resistance in stainless steel components will be readily apparent to those skilled in the art of hydrogen water chemistry. For example, platinum group metals other than palladium can be applied using this technique. A platinum group metal can be injected in the form of an organic or organometallic compound to reduce the electrochemical potential of stainless steel reactor components even in the absence of hydrogen injection. Alternatively, the platinum group metal can be injected in the form of an inorganic compound in conjunction with hydrogen injection to reduce the electrochemical potential of stainless steel reactor components. It may also be possible to dope oxide films on stainless steel components with non-platinum group metals, e.g., zirconium- or titanium-containing acetylacetonates. All such variations and modifications are intended to be encompassed by the claims set forth hereinafter.

I claim:

1. A solution consisting of metal acetylacetonate dissolved in a mixture of ethanol and water, wherein the amount of water in the solution is much greater than the amount of ethanol.

2. The solution as defined in claim 1, wherein said metal is a platinum group metal.

3. The solution as defined in claim 2, wherein said platinum group metal is palladium.

4. A method for manufacturing a solution, comprising the steps of:

dissolving metal acetylacetonate powder in ethanol, said metal having the property of improving the corrosion resistance of oxided stainless steel surfaces when doped therein or coated thereon; and diluting said ethanol solution with water, wherein the amount of water in the solution is much greater than the amount of ethanol.

5. The method as defined in claim 4, wherein said metal is a platinum group metal.

6. The method as defined in claim 5, wherein platinum group metal is palladium.

7. A suspension consisting of metal acetylacetonate powder suspended in a liquid consisting of 100% water.

8. The suspension as defined in claim 7, wherein said metal is a platinum group metal.

9. The suspension as defined in claim 8, wherein said platinum group metal is palladium.

10. A method for manufacturing a suspension, comprising the step of mixing metal acetylacetonate powder in a liquid consisting of 100% water, said metal having the property of improving the corrosion resistance of oxided stainless steel surfaces when doped therein or coated thereon.

11. The method as defined in claim 10, wherein said metal is a platinum group metal.

12. The method as defined in claim 11, wherein said platinum group metal is palladium.

* * * * *